United States Patent
Okamura et al.

(10) Patent No.: US 8,119,420 B2
(45) Date of Patent: Feb. 21, 2012

(54) ABSORPTION PAD FOR IMMUNOASSAY, STRIP FOR IMMUNOASSAY, AND IMMUNOASSAY APPARATUS

(75) Inventors: Chisato Okamura, Tokyo (JP); Minoru Sato, Tokyo (JP)

(73) Assignee: Fujirebio Inc., Tokyo (JP)

( * ) Notice: Subject to any disclaimer, the term of this patent is extended or adjusted under 35 U.S.C. 154(b) by 407 days.

(21) Appl. No.: 12/210,755

(22) Filed: Sep. 15, 2008

(65) Prior Publication Data

US 2009/0053829 A1 Feb. 26, 2009

Related U.S. Application Data

(63) Continuation of application No. PCT/JP2007/054810, filed on Mar. 12, 2007.

(30) Foreign Application Priority Data

Mar. 13, 2006 (JP) .................................. 2006-068239

(51) Int. Cl.
*G01N 33/53* (2006.01)
(52) U.S. Cl. ........ 436/501; 436/514; 436/518; 436/530; 436/810; 435/287.1; 435/287.7; 435/970
(58) Field of Classification Search .................. 436/514, 436/518, 530, 527, 810; 435/287.1, 287.7, 435/970
See application file for complete search history.

(56) References Cited

U.S. PATENT DOCUMENTS

| | | | |
|---|---|---|---|
| 4,810,470 A | 3/1989 | Burkhardt et al. | |
| 5,137,808 A * | 8/1992 | Ullman et al. | 435/7.9 |
| 5,558,834 A | 9/1996 | Chu et al. | |
| 6,605,476 B2 * | 8/2003 | Kobayashi | 436/514 |
| 6,881,378 B1 | 4/2005 | Zimmer et al. | |

FOREIGN PATENT DOCUMENTS

| | | |
|---|---|---|
| EP | 0 303 784 A1 | 2/1989 |
| JP | 64-21361 | 1/1989 |
| JP | 5-209877 | 8/1993 |
| JP | 10-324856 | 12/1998 |
| JP | 11-248701 | 9/1999 |
| JP | 2000-304745 | 11/2000 |
| JP | 3248436 | 11/2001 |
| JP | 2002-012448 | 1/2002 |
| JP | 2002-507725 A | 3/2002 |

(Continued)

OTHER PUBLICATIONS

"Drikette® Desiccant Paper", URL: http://www.fujigel.co.jp/multisorb/drikette.pdf, XP002549523, retrieved on Oct. 9, 2009, 2 pages.

(Continued)

*Primary Examiner* — Bao Thuy L Nguyen
(74) *Attorney, Agent, or Firm* — Oblon, Spivak, McClelland, Maier & Neustadt, L.L.P.

(57) ABSTRACT

Providing an absorption pad which shows remarkable water absorptivity and can shorten a detection time when employed for an immunoassay apparatus. A water absorption pad for the immunoassay apparatus, containing 50% by weight or more of silicon-containing particles wherein a moisture absorptivity is 30% or less at a humidity of 60% or less and a moisture absorptivity is 40% or more at a humidity of 90% or more, a strip for an immunoassay using said absorption pad as a suction part, and an immunoassay apparatus including said strip for the immunoassay.

14 Claims, 7 Drawing Sheets

FOREIGN PATENT DOCUMENTS

| | | |
|---|---|---|
| JP | 3284896 | 3/2002 |
| JP | 2005-503556 | 2/2005 |
| JP | 2005-61910 A | 3/2005 |
| JP | 2005-83927 | 3/2005 |
| WO | WO 94/24563 | 10/1994 |
| WO | WO 99/47930 | 9/1999 |
| WO | WO-03/025573 | 3/2003 |

OTHER PUBLICATIONS

Japanese Office Action issued on May 31, 2011 in corresponding Japanese Application No. 2006-068239 (with an English Translation).

* cited by examiner

ABSORPTION PAD FOR IMMUNOASSAY, STRIP FOR IMMUNOASSAY, AND IMMUNOASSAY APPARATUS

CROSS-REFERENCE TO RELATED APPLICATIONS

This application is a continuation under 35 U.S.C. §120 of PCT/JP2007/054810, filed Mar. 12, 2007 and claims priority under 35 U.S.C. §119 to Japan 2006-068239, filed Mar. 13, 2006. Both of these applications are specifically incorporated by reference in their entireties.

BACKGROUND OF THE INVENTION

1. Field of the Invention

The present invention relates to an absorption pad for an immunoassay, a strip for an immunoassay and an immunoassay apparatus, and particularly relates to an absorption pad for the immunoassay, which is remarkably excellent in water absorptivity, and a strip for the immunoassay and an immunoassay apparatus, which use the absorption pad and shorten a detection time, as well as uses thereof.

2. Description of the Related Art

Analyses of biological components or drugs included in specimens such as blood and urine are important for diagnosis of a pathological condition and determination of a therapeutic process. Thus, an immunoassay apparatus which measures using an antigen-antibody reaction has been used as the apparatus for simply detecting the biological component and the drug.

Conventionally, biological samples collected from the blood, urine and mucosal secretion have been analyzed immunologically in the diagnosis of the pathological condition and the determination of the therapeutic process. An enzyme immunoassay apparatus using the antigen-antibody reaction has been developed as the apparatus used for immunological analyses (see Japan Patent No. 3,248,436; Japan Patent No. 3,284,896; JP 2005-503556-A; JP 2005-83927-A).

In the enzyme immunoassay apparatus, for example, a sandwich complex is formed by antigen-antibody reactions among three, i.e., an antigen or antibody in a specimen, an enzyme-labeled form of an antibody or antigen which reacts with said antigen or antibody, and an antibody or antigen which reacts with said antigen or antibody, and the presence or absence of the complex is detected using a substrate which develops a color by reacting with the enzyme. In these apparatuses, an end corresponding to a downstream of the apparatus is provided with an absorption pad because each component is sequentially dissolved in a developing buffer and the solution is moved in a constant direction in the apparatus (see JP 2005-503556-A).

The absorption pad is made up of an absorptive material, and for example, it has been described that nonwovens made from absorptive filter papers or glass fibers, porous materials and fibrous members are applicable (JP 2005-83927-A).

However, the water absorptivity is insufficient in any absorption pads using the conventional absorptive materials, and it takes some time to detect a result in the apparatus using such a material. Particularly, when the antigen or antibody derived from an infectious disease is subjected to the measurement, it is better that the detection time is as short as possible in terms of rapid treatment and preventing the spread of the infectious disease.

Meanwhile, the conventional immunoassay apparatus is manufactured by individually laminating each member in a cassette, and thus, the water absorptivity can be enhanced by utilizing one having a relatively wide width as the absorption pad. However, in recent years, a laminate system in which all members including the absorption pad are adhered with seals to integrate and then housed in the cassette has been becoming a mainstream. In this case, one having the narrow width is often used as the absorption pad for enhancing production efficiency. Thus, the absorption pad in line with the recent production system, which is remarkably excellent in water absorptivity, has been required.

Here, an ordinarily possible principle as a procedure to shorten the detection time in the immunoassay apparatus may include the enhancement of capillarity by expanding pores in a membrane part where the developing buffer is absorbed and moved. However, when the pores are expanded, a determination line which shows a determination result is not expressed sharply.

BRIEF SUMMARY OF THE INVENTION

In the light of the above problems, it is one object of the present invention to provide an absorption pad which shows the remarkable water absorptivity and can shorten the detection time when employed in an immunoassay apparatus.

As a result of an extensive study, the present inventors have found that the water absorptivity is remarkably enhanced by containing silicon-containing particles which show particular moisture absorptivity in a certain amount or more in an absorptive material also used for the conventional absorption pad.

Furthermore, the present inventors have found that the detection time can be shortened in an immunoassay apparatus using this absorption pad, and that even when using the absorption pad having the narrow width, the detection time can be further shortened compared with the immunoassay apparatus loading the conventional absorption pad having the wide width.

According to the present invention, the absorption pad for the immunoassay, which shows the remarkable water absorptivity, the strip for the immunoassay and the immunoassay apparatus capable of precisely detecting in a short time are provided. Therefore, the present invention contributes to the rapid diagnosis of the pathological condition and the rapid determination of the therapeutic process in infectious diseases.

The present invention includes the following embodiments [1] to [9]:

[1] An absorption pad for an immunoassay comprising 50% by weight or more of silicon-containing particles, the silicon-containing particles having a moisture absorptivity of 30% or less at a humidity of 60% or less and a moisture absorptivity of 40% or more at a humidity of 90% or more;

[2] The absorption pad for an immunoassay according to [1], wherein said silicon-containing particle is silica gel;

[3] A strip for an immunoassay for detecting an antigen and/or antibody in a specimen by an antigen-antibody reaction, comprising:
a labeled form-containing part including a labeled form of an antibody and/or antigen corresponding to the antigen and/or antibody to be detected; and
a suction part composed of the absorption pad according to [1];

[4] The strip for an immunoassay according to [3] further comprising a substrate-containing part including a substrate to said labeled form;

[5] The strip for the immunoassay according to [4] wherein said substrate-containing part is located on another end to one end where the suction part is annexed and said labeled form-containing part is located between the substrate-containing part and the suction part;

[6] An immunoassay apparatus for measuring an antigen and/or antibody in a specimen by an antigen-antibody reaction, comprising the strip for the immunoassay according to [3];

[7] The immunoassay apparatus according to [6] further comprising a developing buffer supply part for supplying a developing buffer to said strip;

[8] An immunoassay method comprising:
measuring an antigen and/or antibody by an antigen-antibody reaction using the strip according to [3]; and

[9] An immunoassay method comprising:
measuring an antigen and/or antibody by an antigen-antibody reaction using the immunoassay apparatus according to [6].

Various modifications and variations of the embodiments described above as well as the concept of the invention will be apparent to those skilled in the art without departing from the scope and spirit of the invention. Although the invention has been described in connection with specific preferred embodiments, it should be understood that the invention as claimed is not intended to be limited to such specific embodiments.

BRIEF DESCRIPTION OF THE DRAWINGS

FIGS. 1-6 use the following reference numbers:
1 Strip for immunoassay
2 Immunoassay apparatus
3 Suction part
4 Labeled form-containing part
5 Substrate-containing part
6 Detection site
7 Mat board (base material)
8 Adhesive tape (seal)
9 Cassette (case)
10 Specimen dropping window
11 Detection window
12 Convex part

DETAILED DESCRIPTION OF THE INVENTION

Figure 1:
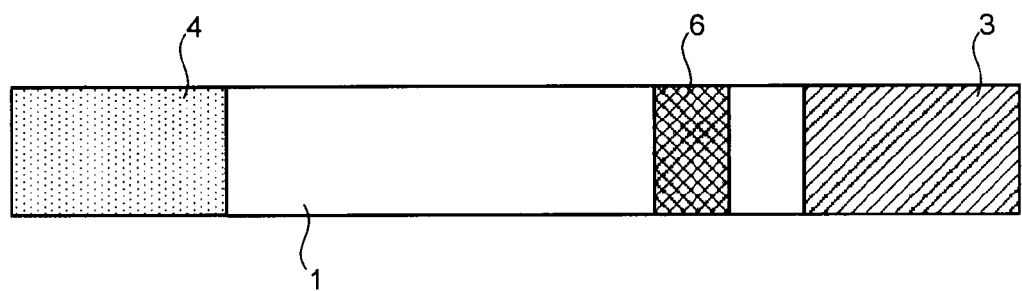
FIG. 1 is a schematic view of one example of an absorption pad for immunoassay of the present invention when viewed from above the surface.

The present invention relates to an absorption pad for an immunoassay, a strip for an immunoassay utilizing the pad, and an immunoassay apparatus, which will be described sequentially below.

(1) Absorption Pad for Immunoassay of the Present Invention

The absorption pad for the immunoassay of the present invention is characterized by containing 50% by weight or more of silicon-containing particles which have a moisture absorptivity of 30% or less at a humidity of 60% or less and a moisture absorptivity of 40% or more at a humidity of 90% or more.

The silicon-containing particle in the present invention means the particle which contains silicon (Si) or a silicon compound(s). The silicon compound means a substance chemically bound to silicon, and may include silicon oxide (quartz, $SiO_2$), silicon nitride ($Si_3N_4$) and silicon carbide (SiC). A ratio of containing silicon or the silicon compound is not particularly limited. A shape thereof is preferably particulate. An average particle diameter of the fine particles depends on a pore volume and desirably smaller in general. Specifically, it is preferably 14 μm or less and more preferably 4.5 μm or less.

An average pore diameter is preferably 25 to 240 angstroms and particularly preferably 70 to 210 angstroms. The pore volume is preferably 0.44 to 1.80 mL/g and particularly preferably 0.80 to 1.60 mL/g. These ranges include all intermediate subranges and values, for example, the lower end point of the average pore diameter may be 25, 30, 35, 40, 45, 50, 55, 60, 66, 70, 80, 85, 90, 100, 125, 150, 200 angstroms, and the upper end point may be 240, 230, 220, 210, 200, 190, 180, 170, 160, 150, 140, 130, 120, 110, 100, 90, 80, or 75 angstroms. The lower end point of pore volume may be 0.44, 0.45, 0.50, 0.55, 0.60, 0.65, 0.75, 0.85, 0.95, 1.00, 1.10, 1.20, 1.30, 1.40, 1.50, 1.60, 1.70 or 1.75 mL/g, and the upper end point may range down from 1.80, 1.75, 1.70, 1.65, 1.60, 1.55, 1.50, 1.45, 1.40, 1.35, 1.30, 1.25, 1.20, 1.10, 1.00, 0.95, 0.90, 0.85, 0.75, 0.70, 0.65, 0.60, 0.55, 0.50, or 0.45 mL/g.

Silica gel is preferable as such a silicon-containing particle. The silica gel is the gel of silicon oxide ($SiO_2$) and a porous powder. The silica gel preferably used in the present invention may include those exhibiting rough aggregation of particles and having the large particle diameters, small surface areas and the large pore volumes. More specifically, B shaped silica gel in accordance with JIS Z 0701 is preferable. That is, those having a moisture absorption capacity of 3.0% or more, 10.0% or more or 50.0% or more at a relative humidity of 20%, 50% or 90%, respectively, a water content percentage of 2.5% or less, a pH value of 4 to 8, a specific resistance of 3,000 Ω·cm or more and 98% or more silic acid anhydrate in the components can be preferably used. These ranges include all intermediate subranges and points.

In the present invention, it is necessary to use the silicon-containing particles which show the moisture absorptivity of 30% or less at a humidity of 60% or less and the moisture absorptivity of 40% or more at a humidity of 90% or more. Preferably, the silicon-containing particles which show the moisture absorptivity of 20% or less at a humidity of 60% or less and the moisture absorptivity of 70% or more at a humidity of 95% or more may be included. These ranges include all intermediate subranges and values. For example, the moisture absorptivity at a humidity of 60% or less may be 30%, 29%, 28%, 27%, 25%, 22%, 20%, 15%, 12.5%, 10%, 5%, 2.5% or less. The moisture absorptivity at a humidity of 90% or 95% or more includes 40%, 41%, 42%, 45%, 50%, 52.5%, 55%, 60%, 65%, 70%, 75%, 80%, 85%, 89%, 90%, 95% or more.

When the moisture absorptivity departs from the aforementioned range, the moisture is absorbed before starting the immunoassay and it is likely to prevent the detection time from being shortened in the actual immunoassay. Meanwhile, a lower limit of the moisture absorptivity can be appropriately set up within the range in which the function as the absorption pad is sufficiently exerted upon immunoassay reaction.

The water absorptivity can be obtained by multiplying 100 to a numerical value obtained by dividing a value by subtracting a dry mass (dry weight) of silica gel from a moisture absorption mass (moisture absorption weight) of silica gel by the dry mass (dry weight) of silica gel.

The absorption pad of the present invention is necessary to contain 50% by weight or more of the silicon-containing particles as described above in dry weight. When a containing rate is less than 50% by weight, the water absorptivity becomes insufficient and the improvement of the detection time is less observed.

The material for the absorption pad is not particularly limited as long as it has the water absorptivity, and can be composed of, for example the materials made up of natural or synthetic polymer compounds such as porous materials of polyvinyl alcohol (PVA), nonwovens and cellulose, sponges and filter papers alone or in combination. A size and a thickness of the absorption pad is not limited, but it is typically preferable for measuring efficiently to use the pad having a longitudinal and transversal lengths of about 3 mm to 15 mm and the thickness of about 0.5 mm to 4 mm. These ranges include all intermediate subranges and values. A method for manufacturing such an absorption pad is not particularly limited, and the pad can be manufactured, for example, by mixing a raw material (e.g., filter paper) and the silicon-containing particles (silica gel) in an organic solvent and then evaporating the organic solvent.

Such an absorption pad for the immunoassay of the present invention is useful as the absorption pad of the strip for the immunoassay. The strip for the immunoassay is a device for immunologically measuring the antigen and/or the antibody in the specimen utilizing the antigen-antibody reaction. Measurement methods utilizing the antigen-antibody reaction may include enzyme immunoassays (EIA), immunochromatography and immunoblotting.

Those which are preferable as the strip for the immunoassay using the absorption pad of the present invention are those described below.

(2) Strip for Immunoassay of the Present Invention

The strip for the immunoassay means a strip for immunologically measuring a particular substance in the specimen. The material for the strip for the immunoassay can be appropriately selected from the materials in which the specimen, the labeled form, the substrate and the developing buffer can be permeated and moved, and particularly the material capable of running the solution by a capillary action is preferable. For example, water absorptive materials used as membrane materials may be included. Specifically, the material may include filter papers and porous membranes formed from cellulose such as cellulose and nitrocellulose or derivatives thereof, or glass fibers. The strip can also be used by blocking a part thereof with bovine serum albumin (BSA), casein or sucrose in order to prevent the adsorption due to non-specific reactions of proteins.

The shape and the size of the strip for the immunoassay are not limited, and it is possible to make, for example, the strip having the width of about 3 to 10 mm and the length of about 30 to 100 mm. Particularly, it is also possible to make a longer and thinner shape in the strip for the immunoassay of the present invention because the absorption pad described in the above (1) is annexed as a suction part. The thickness of the strip is preferably 100 µm to 1 mm. It is also possible to make the thickness relatively thin because it is not necessary to impregnate the solution in as large amount as the suction part and the substrate-containing part described later.

The strip for the immunoassay of the present invention is made by annexing the suction part made up of the absorption pad described in the aforementioned (1).

The suction part is a water absorptive member to make the permeation of the antigen, the antibody and the specimen into the strip and the movement thereof in the strip easy, and it is necessary to use the aforementioned absorption pad as the suction part in the present invention. This enables to enhance a detection sensitivity of a trace component in the specimen and analyze the specimen solutions in large amounts.

The shape and the size of the suction part are not particularly limited, but it is preferable to make the size capable of being placed on the strip. To cite one example, it is preferable to make the width 1 to 10 mm and particularly 4 to 6 mm. It is preferable to make the length 10 to 50 mm and particularly 13 to 17 mm. It is preferable to make the thickness 0.5 to 2 mm and particularly 0.7 to 1.2 mm. These ranges include all intermediate subranges and values.

In the present invention, the aforementioned absorption pad excellent in absorptivity is used as the suction part. Thus, even when the smaller thin and long shape is used, the excellent absorptivity can be exerted and the detection time can be made shorter.

A position of the suction part on the strip is not particularly limited as long as the specimen and the labeled form move in the particular direction in the strip upon detection by the action of the suction part, but it is preferable that the suction part is annexed at one end of the strip. The absorption pad as the suction part can be annexed to the strip with the adhesive tape or a laminate by a hot melt agent as needed.

The strip for the immunoassay of the present invention comprises the labeled form-containing part which contains the labeled form of the antibody and/or antigen corresponding to the antigen and/or antibody to be detected. By containing the labeled form, the detection of the specimen becomes easy because the labeled form is sucked together with the specimen by the suction part within the strip and forms the complex together with the specimen. When an enzyme labeled form is used as the labeled form, the detection of the specimen becomes still easier because the enzyme labeled form is bound to the substrate to form a substrate-bound labeled form and the specimen and the substrate-bound labeled form builds a sandwich complex.

The labeled form means one obtained by binding some sort of label to the antibody and/or antigen corresponding to the antigen and/or antibody to be detected. That is, when the antigen is subjected to the detection, the labeled form of the antibody corresponding thereto is contained, and when the antibody is subjected to the detection, the labeled form of the antigen corresponding thereto is contained. It is also possible to contain two or more antibodies and antigens.

The method for manufacturing the labeled antibody and/or antigen is not particularly limited as long as they exhibit the antigen-antibody reaction to the antigen and/or antibody to be detected. For example, the antibody and/or antigen obtained by cell culture using standard methods can be utilized, and the recombinant antibody and/or antigen obtained by gene recombination can also be used. Also, a fusion antigen produced by fusing two or more antigens, antibody fragments such as Fab fragments and F(ab)$_2$ fragments, and haptens may be used.

Examples of the label may include enzymes, radioisotopes, latexes, metal colloid particles, fluorescent particles and colored particles.

The enzyme may include various enzymes conventionally used for the enzyme immunoassays (EIA). Examples thereof may include alkaline phosphatase, peroxidase and β-D-galactosidase. Examples of the radioisotope may include isotopes of iodine, tritium and carbon. For example, it is possible to label using the method using Bolton Hunter reagents.

Examples of the latex may include particles of polymer compounds such as polystyrene latex. The metal colloid particle is the particle made up of various metal colloids. Examples thereof may include the particles made up of the metal colloids of selenium, platinum and gold. The particle diameter of the particle is preferable 10 nm to 1 μm.

The fluorescent particle means the particle which emits the fluorescence, and examples thereof may include the particles of polystyrene, styrene-butadiene copolymers, styrene-acrylic acid copolymers and glass containing fluorescent substances such as fluorescein, rhodamine and platinum cyanide. The colored particle is the particle composed of an organic polymer compound or an inorganic compound colored with various dyes and pigments, and for example composed of the material obtained from polystyrene, polymethyl acrylate, polyacrylamide, polypropylene, polycarbonate and glass alone or in mixture. The particle diameter of the fluorescent particle and the colored particle is preferably 10 nm to 1 μm.

The labeled antibody and/or antigen can be produced by forming a covalent bond or a non-covalent bond between the antibody and/or antigen and the label by the standard method. Specifically, it is possible to utilize a glutaraldehyde method, a periodic acid method, a maleimide method, a pyridyl disulfide method and methods using various crosslinkers (e.g., see Proteins, Nucleic Acids and Enzymes, Suppl. vol. 31: 37-45, 1985). Examples of the crosslinker which can be used in binding methods using the crosslinker may include N-succinimidyl-4-maleimidobutyrate (GMBS), N-succinimidyl-6-maleimidohexanoate and N-succinimidyl-4-(N-maleimidomethyl)cyclohexane-1-carboxylate.

When the covalent bond is formed, a functional group present in the antigen or antibody can be used, and additionally, the functional group such as a thiol group, an amino group, a carboxyl group or a hydroxyl group is previously introduced, and then the labeled one can be produced by the above binding method. The method for forming the non-covalent bond may include a physical absorption method.

The position of the labeled form-containing part on the strip is not particularly limited, and may be any position other than the end at which the suction part is annexed. For example, such position can also be the other end to the end at which the suction part is annexed, or can be located at a central part (between the suction part and the substrate-containing part) when the substrate-containing part described later is provided.

The labeled form-containing part can be formed by containing the dry labeled form in a main body of the strip or in a distinct absorptive material as a labeled form-containing pad. The amount of the labeled form contained in the labeled form-containing part can be appropriately changed depending on whether the labeled form-containing part is a part of the strip or the distinct member or depending on the type of the antibody and/or antigen subjected to the examination and the amount of specimen used for the measurement, and is typically about 0.01 to 5 μg in dry weight.

When the labeled form is contained in the main body of the strip, the strip can be lightened as well as this can be easily manufactured. In this case, it is preferable to contain one labeled with the latex or the metal colloid as the labeled form.

Meanwhile, by annexing the absorptive material distinct from the strip as the labeled form-containing pad on the strip, it is possible to contain the labeled form sufficiently, smoothly move the developing buffer in the strip and perform the precise immunoassay with high sensitivity in a short time even when the specimen in large amount is used. The absorptive material is preferably one containing the labeled form in large amount, and examples thereof may include materials made up of natural or synthetic polymer compounds such as porous materials of polyvinyl alcohol (PVA), nonwovens and cellulose, sponges and filter papers. These can be used alone or in combination.

The shape and the size of the labeled form-containing pad are not particularly limited, and can be made into a strip shape having the size capable of being placed on the strip. Typically those having the width of 1 to 10 mm, the length of 3 to 30 mm and the thickness of 0.5 to 2 mm can be used. The labeled form-containing pad can be placed on the strip with the adhesive tape or the laminate by the hot melt agent as needed.

The strip for the immunoassay of the present invention may further comprise the substrate-containing part which contains the substrate for the labeled form of the antibody and/or antigen. In particular when the labeled form contained in the strip is the enzyme labeled form, taking such a constitution is preferable because the substrate for the enzyme is previously contained in the substrate-containing part to make the detection simple.

Upon detecting using the strip for the immunoassay, the substrate is typically supplied to the strip by adding and dissolving it in the developing buffer containing the specimen. Thus, the substrate can also be contained in a state where the substrate is dissolved in the developing buffer. However, in terms of reducing the amount of the developing buffer required, preventing the change with time of determination results and enhancing storage stability, it is preferable to contain only the substrate in the strip.

The substrate means the substance specifically bound to the enzyme, and those corresponding to the labels can be appropriately selected and used. Describing the substrate as one example when the enzyme is used as the label, those which are bound to the enzyme to develop the color or emit the light, e.g., coloring substrates, fluorescent substrates and luminescent substrates can be used. Specific examples of the coloring substrate, the fluorescent substrate and the luminescent substrate may include the followings corresponding to the enzymes to be used.

As the coloring substrate, 2,2'-azino-bis(3-ethylbenzothiazoline-6-sulfonic acid) (ABTS), 3,3',5,5'-tetramethylbenzidine (TMB) or diaminobenzidine (DAB) in combination with hydrogen peroxide can be used when peroxidase is used as the enzyme. When alkaline phosphatase is used, 5-bromo-4-chloro-3-indolyl-phosphate (BCIP) can be used.

Meanwhile, as the fluorescent substrate, 4-methylumbelliferyl phosphate (4MUP) can be used when alkaline phosphatase is used as the enzyme. When β-D-galactosidase is used, 4-methylumbelliferyl-β-D-galactoside (4MUG) can be used.

Furthermore, as the luminescent substrate, a disodium salt of 3-(2'-spiroadamatane)-4-methoxy-4-(3''-phosphoryloxy)phenyl-1,2-dioxetane (AMPPD) can be used when alkaline phosphatase is used as the enzyme. When β-D-galactosidase is used, 3-(2'-spiroadamatane)-4-methoxy-4-(3''-β-D-galactopyranosil)phenyl-1,2-dioxetane (AMGPD) can be used. When peroxidase is used, luminol or isoluminol in combination with hydrogen peroxide can be used.

A content of the substrate can be appropriately determined depending on various conditions e.g., types of the enzyme and the substrate to be used and the specimen to be subjected, and can be typically 50 to 200 μg.

The position of the substrate-containing part on the strip is not particularly limited, and may be any position other than the end at which the suction part is annexed. For example, the substrate-containing part can be located on the other end side to the end at which the suction part is annexed, and preferably on the other end. It can be located on the central part (between the suction part and the substrate-containing part).

The substrate can be contained in the strip for the immunoassay by adding the substrate dissolved in a solution to the strip or the other absorptive material and drying it.

The substrate may be contained in any part of the strip, or a substrate-containing pad obtained by containing the substrate in the other absorptive material can also be annexed on the strip for the immunoassay. When the substrate is contained as a part of the strip, the substrate can be directly dropped onto the strip. Meanwhile, when the substrate is annexed as the substrate-containing pad, the absorptive pad containing the substrate may be annexed. As the absorptive pad, the absorptive member described in the aforementioned strip can be directly utilized. The size of the substrate-containing pad can be appropriately set up based on the types of the specimen, the developing buffer or the sizes of respective parts. Typically those having the width of 1 to 10 mm, the length of 10 to 50 mm and the thickness of 0.5 to 2 mm can be used. The substrate-containing pad can be annexed to the strip the adhesive tape or the laminate by the hot melt agent as needed.

In the strip for the immunoassay, the specimen is dropped on any part of its surface upon the immunoassay. A site to which the specimen is dropped may be any part of the surface of the strip, and the site at which the labeled form contained in the strip can be bound to the specimen can be appropriately selected.

In the strip for the immunoassay, it is possible to form a detection site for identifying whether the antigen and or antibody to be detected is present in the specimen or not.

The detection site can be formed by immobilizing the antibody and/or antigen corresponding thereto to the surface of the strip. It can be immobilized by chemical bond such as covalent bond, or physical absorption.

Also, the antibody and/or antigen corresponding to the antigen and/or antibody to be detected is bound to an insoluble carrier, and this may be contained in the strip. The insoluble carrier may include particles obtained by insolubilizing the mixture composed of gelatin, gum arabic and sodium hexametaphosphate (see JP Sho-63-29223-B), such as polystyrene latexes, various animal erythrocytes and glass fibers. The insoluble carrier can be bound to the antibody and/or antigen by the chemical bond or the physical absorption. The shape of the detection part can be various shapes such as linear and circular shapes. Among them, the linear shape by forming to orthogonalize with the direction of running e.g., the specimen, the substrate and the developing buffer is preferable because the detection sensitivity can be enhanced.

The method for producing the antigen and/or antibody immobilized to the detection site is not limited, and those included in the description for the labeled form-containing part can be utilized. Multiple types of the antigens and/or antibodies can be immobilized. In this case, by immobilizing each antigen and/or antibody to the different position on the strip, it is possible to distinctively detect (e.g., as two determination lines) the antibody and/or antigen corresponding to each antigen and/or antibody. Meanwhile, by mixing and immobilizing respective antigens and/or antibodies, it is also possible to detect the antibodies and/or antigens corresponding to respective antigens and/or antibodies with no distinction.

The position of the detection site is not particularly limited as long as the position is the surface of the strip, but it is preferable to provide it adjacent to the suction part.

Figure 2:
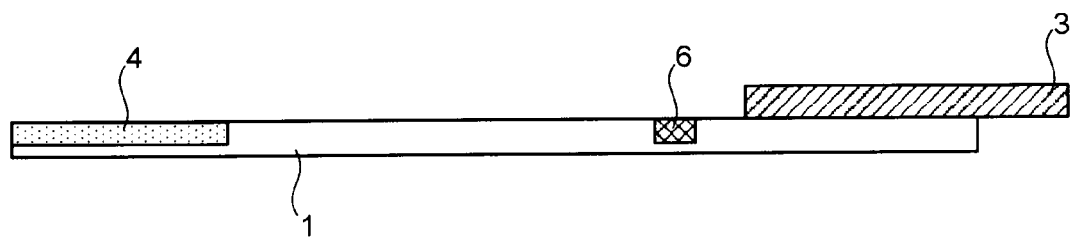
FIG. 2 is a schematic view of one example of an absorption pad for immunoassay of the present invention when viewed from a side.

One of examples of the strip for the immunoassay of the present invention is shown in FIGS. 1 to 2. FIG. 1 is a schematic view of one example of the strip for the immunoassay of the present invention when viewed from the upper surface. In a device in FIG. 1, a suction part 3 is placed on one end of the strip 1, and another end is provided with a labeled form-containing part 4. Further, a detection site 6 is provided to locate in the region sandwiched with the suction part and the labeled form-containing part.

Figure 3:
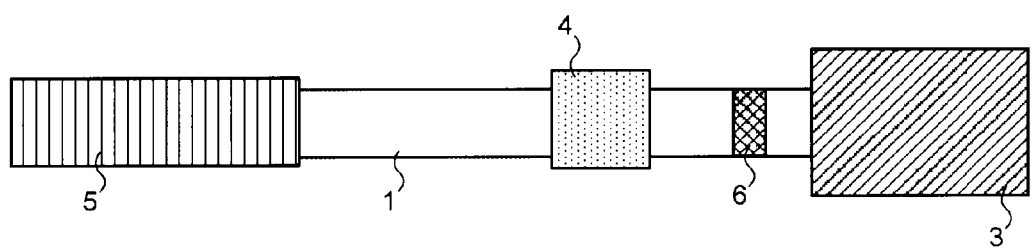
FIG. 3 is a schematic view of one example of an absorption pad for immunoassay of the present invention when viewed from above the surface.
Figure 4:
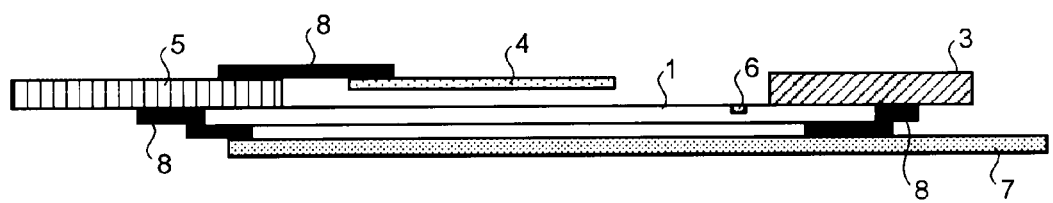
FIG. 4 is a schematic view of an example of an absorption pad for immunoassay of the present invention when viewed from the side.
Figure 5:
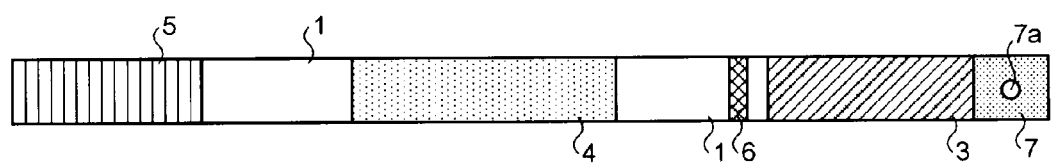
FIG. 5 is a schematic view of the apparatus in FIG. 4 when viewed from a top.

Meanwhile, other examples of the strip for the immunoassay of the present invention when the substrate-containing pad is annexed are shown in FIGS. 3 to 5.

FIG. 3 is a schematic view of one example of the strip for the immunoassay of the present invention when viewed from the upper surface. In the apparatus in FIG. 3, one end of the strip 1 is provided with the suction part 3, and a substrate-containing part 5 as another member (substrate-containing pad) is placed on another end. The labeled form-containing part 4 is placed as another member (labeled form-containing pad) on the central part. The detection site 6 is provided between the labeled form-containing part 4 and the suction part 3. The width of the suction part 3 is wider than the width of the strip 1, and the widths of the labeled form-containing part 4 and the substrate-containing part 5 are slightly wider than that of the strip 1.

FIG. 4 is a schematic view of still another example of the immunoassay apparatus of the present invention when viewed from the side. FIG. 5 is a schematic view of the apparatus in FIG. 4 when viewed from the top.

The apparatus in FIG. 4 takes the same component as in FIG. 3, but a mat board 7 is provided under the strip 1, and an adhesive tape (seal) 8 connects between the mat board 7 and the strip 1 and the suction part 3, between the mat board 7 and the strip 1 and the substrate-containing part 5 and between the substrate-containing part 5 and the labeled form-containing part 4. The length of the mat board 7 is slightly longer than the length of the suction part 3.

The strip for the immunoassay can also be used by laminating and fixing onto a support member such as plastics, metals and papers depending on the type of the label.

In the strip for the immunoassay, by supplying the specimen mixed with the developing buffer onto the strip if necessary, it is possible to examine the presence or absence of the desired antibody or antigen in the specimen. For example, in the examples in FIGS. 1 and 2, the specimen diluted with the developing buffer can be supplied using a pipette to the labeled form-containing part to perform the subsequent operation. In the examples in FIGS. 3 to 5, the substrate-containing part can also be immersed in a container containing the developing buffer upon starting the measurement.

The specimen in the present invention means a sample which may be subjected to the immunoassay. Examples of specimen may include various biological samples such as serum, plasma, whole blood, urine and mucosal secretions (nasal cavity suction fluids, pharynx wiping fluids, nasal cavity wiping fluids).

The developing buffer is not particularly limited as long as it is a liquid in which the antibody and the antigen are soluble, various buffers can be used, and surfactants and buffering agents can be contained appropriately if necessary. The buffers including the buffering agents may include acetate buffer, borate buffer, tris-hydrochloride buffer and diethanolamine buffer. The content of the developing buffer and a dilution rate of the specimen can be appropriately set up depending on the substrate and a composition of the developing buffer.

Such a strip for the immunoassay of the present invention is useful as the immunoassay apparatus, and the present invention also provides such an immunoassay apparatus as described in the following (3).

(3) Immunoassay Apparatus of the Present Invention

The immunoassay apparatus means the apparatus for measuring the antigen and/or antibody in the specimen by the antigen-antibody reaction, and is characterized by including the aforementioned strip for the immunoassay.

The immunoassay apparatus of the present invention can take the component in which the aforementioned strip for the immunoassay is housed in a cassette (case or container). The shape of the cassette may be the shape which supports and protects the aforementioned respective parts. In the cassette, a detection determination window for observing the reaction of the specimen in the detection site in the strip and a specimen dropping window for dropping the specimen can be provided in order to make the dropping of the specimen and the determination of the specimen easy.

The specimen is typically dissolved in the developing buffer and then supplied to the strip for the immunoassay in the cassette, a developing buffer supply part for supplying the developing buffer to the strip for the immunoassay can also be provided in the cassette.

The developing buffer can be supplied to the strip by immersing the developing buffer supply part in the container containing the developing solvent upon starting the measurement, or by using a dropping pipette. However, a developing buffer housing part which houses the developing buffer is provided separately, and the measurement can be started by breaking down the housing part upon stating the measurement.

The developing buffer housing part may be a liquid bath which can house the developing buffer, and preferably has the structure which can be broken down by shock to supply the developing buffer to the developing buffer supply part. For example, the developing buffer housing part can have the structure which is the container having an opening, in which the developing buffer is accumulated and the opening is covered with a breakable film such as metal foil such as aluminium film or a thin plastic film which can be easily broken down with fingers.

Furthermore, the position of the developing buffer housing part can be typically the position adjacent to the strip for the immunoassay, and is preferably the position adjacent to the substrate-containing part when the substrate-containing part is provided on the strip. By making this way, the liquid bath can be broken down and the developing buffer can be contacted with the strip upon starting the measurement.

In terms of making the supply of the developing buffer from the developing buffer housing part to the strip easy, it is preferable that an upper part of the developing buffer housing part is provided with a convex part, and a projection for breaking down the film on the opening in the aforementioned developing buffer housing part is arranged within the convex part. Furthermore, it is possible to take the structure in which the upper side of the water absorption part is provided with an evaporation window for evaporating the developing buffer.

The material of the cassette is not particularly limited, and is preferably a plastic in terms of flexibility and easiness of handling.

When the immunoassay apparatus is made by including the strip for the immunoassay in the cassette, in the case of using the strip for the immunoassay where the members are not joined with the adhesive tape as the aforementioned form in FIG. 3, the product can be provided by imbedding and fixing each member in the cassette. Meanwhile, the members can be integrally imbedded in the cassette by connecting respective members with the adhesive tape 8 shown in FIG. 4. In this case, by matching the width of the suction part 3 to the width of the strip 1, it is possible to make the manufacture of the apparatus easy as well as effectively leverage the materials to manufacture the product in large amounts. By providing the mat board 7 with holes 7*a*, it becomes easy to load the cassette because pins on the cassette fit into the holes 7*a*.

Figure 6:
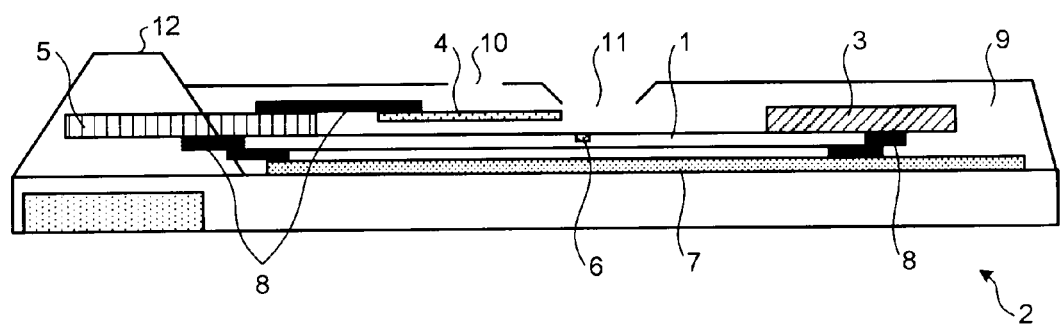
FIG. 6 is a schematic view of an immunoassay apparatus comprising a cassette when viewed from the side.

An example of the immunoassay apparatus comprising the cassette is shown in FIG. 6. In the apparatus 2 in FIG. 6, when the convex part 12 is pushed, the convex part is deformed and the internal projection (not shown in the figure) breaks down the subjacent developing buffer housing part (not shown in the figure) to supply the developing buffer to the substrate-containing part 5. A specimen dropping window 10 is provided for dropping the specimen on the strip, and a detection window 111 is provided on the detection site 6.

This way, the immunoassay apparatus of the present invention can measure the antigen and/or antibody in various specimens by the antigen-antibody reaction. That is, the immunoassay apparatus can be used for the purposes of examining whether the particular antigen and/or antibody is contained in the specimen or not (detection), specifying the type of the antigen and/or antibody contained in the specimen (identification) and measuring the amount of the antigen and/or antibody contained in the specimen (quantification). The specimens are the same as the specimens described for the pad for the immunoassay.

One example of immunoassay methods using the immunoassay apparatus of the present invention will be described in more detail as follows.

First, the specimen (e.g., serum and the like) is supplied to the apparatus (e.g., labeled form-containing part). When the supplied specimen contains the antigen and/or antibody subjected to the measurement, this antigen and/or antibody is reacted with the labeled form of the antibody and/or antigen contained in the strip in the immunoassay apparatus to form the complex.

Meanwhile, when the developing buffer is supplied to the apparatus in the state of mixing with the specimen or separately from the specimen simultaneously or sequentially with the specimen supply, the developing buffer allows the complex to permeate the strip as well as to move toward the suction part side by capillary phenomenon. When the substrate is contained in the strip, the developing buffer allows the label (e.g., enzyme) in the complex to bind to the substrate, and allows this bound form to move toward the suction part side by capillary phenomenon. When the complex or the bound form is moved with the developing buffer in the strip to reach the detection site, the complex or the bound form with the substrate and the antigen and/or antibody in the specimen are trapped by the antibody and/or antigen immobilized to the detection site, and remain on the detection site. As a result, the complex or the bound form develops the color or emits the light. Thus the color or the light can be identified on the detection site. The components and the developing buffer which were not trapped in the detection site are absorbed in the suction part.

On the contrary, when the specimen does not contain the antigen and/or antibody subjected to the measurement, no complex with the labeled form is formed, thus, nothing is trapped by the antibody and/or antigen immobilized to the detection site, and the specimen and the like are absorbed in the suction part. Therefore, neither color nor light is observed on the detection site.

The method for observing the developed color or the emitted light can be appropriately set depending on the type of label, and a measurement apparatus such as a scintillation counter, a calorimeter, a fluorophotometer, a photon counter and a sensitized film can be used as well as visual observation. For example, the method, in which the enzyme is used as the label and the presence or absence of the dye (determination line) produced by the color developing substrate is qualitatively measured by visual observation, is simple. In this case, a semi-quantitative analysis becomes possible by using a color chart corresponding to the concentrations of the antibody.

EXAMPLES

The present invention will be described in more detail with reference to the following Examples.

Measurement of Water Absorption Amount in Absorption Pad with Silica Gel

In the following Examples 1 to 2 and Comparative Examples 1 to 2, immunoassay apparatuses using the absorption pad containing a different content of silica gel were prepared, and relevance between silica gel content and a water absorption amount in the absorption pad was examined by measuring the water absorption amount in the absorption pad in each apparatus.

Example 1

An absorption pad (length: 15 mm, width: 5 mm, thickness: 1 mm supplied from Azumi Filter Paper Co., Ltd.) with silica gel containing 50% by weight of silica gel (% in dry weight. "%" which represents a content rate of silica gel in the absorption pad herein denotes % in the dry weight) was prepared. An immunoassay apparatus shown in FIG. 6 was made by laminating this absorption pad to a membrane as a strip and absorptive members as a labeled form-containing part and a substrate-containing part with seals, attaching the membrane to a mat board and fixing this in a cassette. A nitrocellulose membrane (length: 50 mm, width: 5 mm, thickness: 0.25 mm) was used as the strip for the immunoassay in the immunoassay apparatus. As the labeled form, an alkaline phosphatase (Alp)-labeled anti-influenza antibody was used, the antibody was dissolved in a solution containing BSA (containing 1 to 0.5%), casein treated with alkali (containing 1 to 0.5%), a surfactant (Triton X-100) and sucrose, the antibody solution was dropped on the absorptive member (made from polyvinyl alcohol, length: 21 mm, width: 5 mm, thickness: 0.5 mm), which was then dried and used as the labeled form-containing part. Furthermore, 20 mM disodium 5-bromo-4-chloro-3-indolyl-phosphate salt (BCIP, Na) was used as the substrate. The buffer at pH 9.8 composed of 0.1 M 2-amino-2-methyl-1-propanol, 1 mM magnesium chloride, 0.05% sodium azide and 0.001% sodium dodecylbenzene-sulfonate (SDBS) was used as the developing buffer. These were laminated with the seals (ARCare7815).

Figure 7:
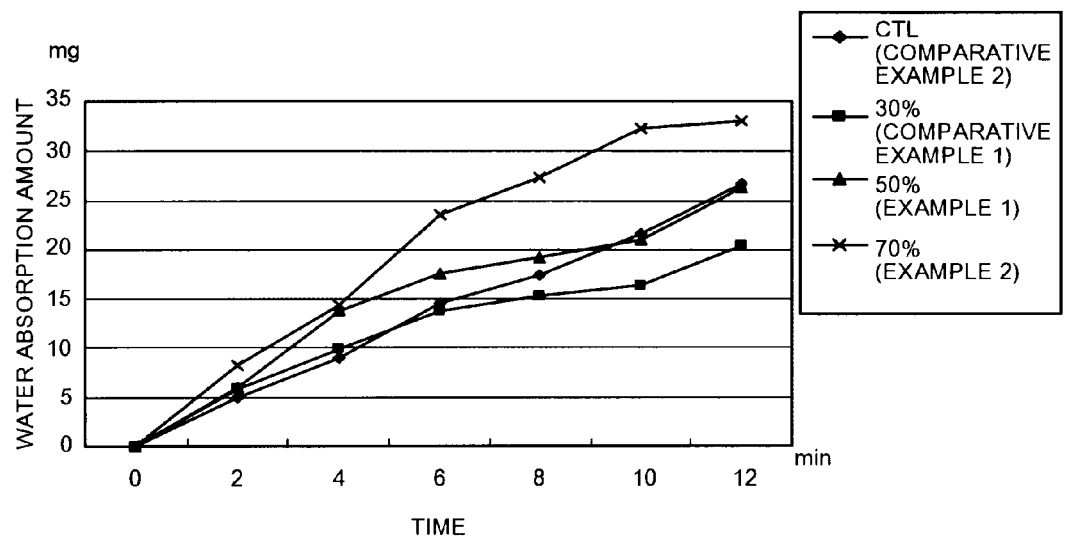
FIG. 7 is a view showing changes with time of water absorption amounts in absorption pads in immunoassay apparatuses in Examples 1 and 2 and Comparative Examples 1 and 2.

30 μL of a specimen-diluted solution (tris buffer containing 0.095% sodium azide, the surfactant and BSA) was added onto a specimen dropping part, and the developing buffer was supplied by pushing a convex part of the cassette. The absorption pad was removed and weighed after 2, 4, 6, 8, 10 and 12 minutes to calculate a difference from the weight before the absorption as the water absorption amount. Changes with time of the water absorption amounts in the absorption pad are shown in FIG. 7.

Example 2

The test was performed in the same way as in Example 1 except for using one containing 70% by weight of silica gel (length: 15 mm, width: 5 mm, thickness: 1 mm supplied from Azumi Filter Paper Co., Ltd.) as the absorption pad with silica gel. The changes with time of the water absorption amounts in the absorption pad are shown in FIG. 7.

Comparative Example 1

The test was performed in the same way as in Example 1 except for using one containing 30% by weight of silica gel (length: 15 mm, width: 5 mm, thickness: 1 mm supplied from Azumi Filter Paper Co., Ltd.) as the absorption pad with silica gel. The changes with time of the water absorption amounts in the absorption pad are shown in FIG. 7.

Comparative Example 2

The test was performed in the same way as in Example 1 except that wine filter paper (product name: wine filter paper, supplied from Whatman Japan, length: 15 mm, width: 10 mm, thickness: 1 mm) was used in place of the absorption pad with silica gel. The changes with time of the water absorption amounts in the absorption pad are shown in FIG. 7.

For the water absorption amounts in respective apparatuses in Examples 1 to 2 and Comparative Examples 1 to 2, it was found from FIG. 7 that the amount in the apparatus using the absorption pad containing 30% by weight of silica gel (Comparative Example 1) was smaller than that in the control apparatus (Comparative Example 2), but that the amount in the apparatus using the absorption pad containing 50% by weight of silica gel (Example 1) was slightly larger than that in the control apparatus (Comparative Example 2) although the size of the absorption pad is smaller than that of the filter paper, and that the amount in the apparatus using the absorption pad containing 70% by weight of silica gel (Example 2) was much larger than that in the control apparatus (Comparative Example 2).

From these results, it has been demonstrated that the immunoassay apparatus using the absorption pad containing 50% by weight or more of silica gel is excellent in water absorptivity and can shorten the detection time.

Sensitivity Test of Silica Gel-Containing Absorption Pad

In the following Examples 3 to 4 and Comparative Examples 3 to 4, immunoassay apparatuses using the absorption pad containing the different content of silica gel were prepared, and the relevance of the silica gel content and the detection time in the absorption pad was examined by measuring the detection time in each apparatus.

Example 3

The absorption pad with silica gel containing 50% by weight of silica gel (same as Example 1) was prepared, and the laminate was enclosed in a white cassette to make the immunoassay apparatus shown in FIG. 6.

The immunoassay apparatus was made by the same way as in Example 1 using the nitrocellulose membrane as the strip and using the same labeled form-containing part, substrate, developing buffer and seal as those in Example 1.

Figure 8:
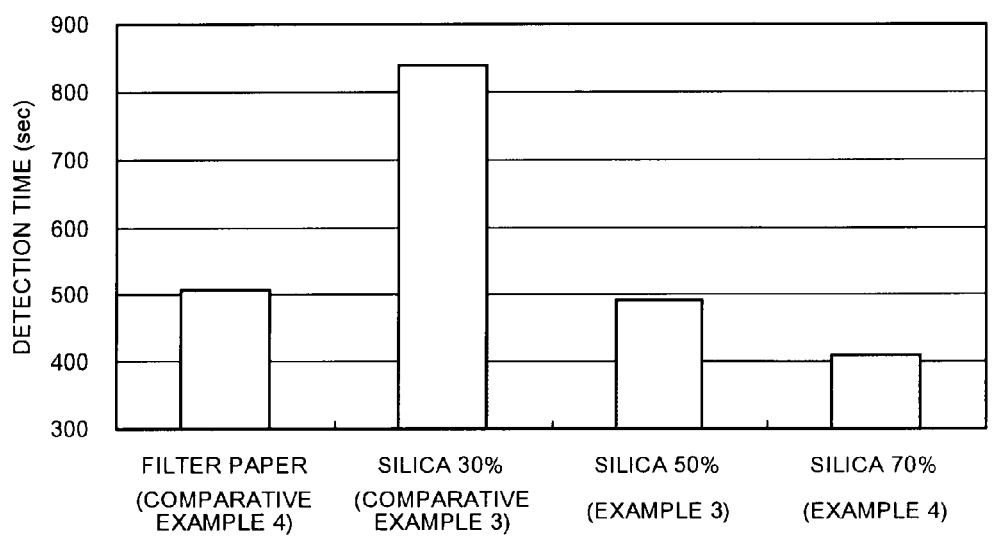
FIG. 8 is a view showing detection times in immunoassay apparatuses in Examples 3 and 4 and Comparative Examples 3 and 4.

30 µL of a specimen obtained by diluting recombinant A type and B type influenza antigens with the specimen-diluted solution in the above Example 1 into 0.8 to 6.4 million times was added onto the specimen dropping part, the developing buffer was supplied by pushing the convex part of the cassette, and the time until the determination line was displayed on the detection site was measured. This was rendered the detection time. In a detection condition, a temperature was 25.1 to 25.5° C. and humidity was 55 to 57%. The time required for the detection (detection time) is shown in FIG. 8.

Example 4

The test was performed in the same way as in Example 3 except for using one containing 70% by weight of silica gel (same one as Example 2) as the absorption pad with silica gel. The changes with time of the water absorption amounts in the absorption pad are shown in FIG. 8.

Comparative Example 3

The test was performed in the same way as in Example 3 except for using one containing 30% by weight of silica gel (same one as Comparative Example 1) as the absorption pad with silica gel. The detection time is shown in FIG. 8.

Comparative Example 4

The test was performed in the same way as in Example 3 except that the wine filter paper was used in place of the absorption pad. The detection time is shown in FIG. 8.

As is evident from FIG. 8, the detection time in the apparatus using the absorption pad containing 30% by weight of silica gel (Comparative Example 3) was widely prolonged compared with that in the apparatus using the filter paper, which was the control (Comparative Example 4). On the contrary, the detection time in the apparatus using the absorption pad containing 50% by weight of silica gel (Example 3) was slightly shortened compared with the control, and the detection time in the apparatus using the absorption pad containing 70% by weight of silica gel (Example 4) was much shortened.

From these results, it has been demonstrated that the immunoassay apparatus using the absorption pad containing 50% by weight or more of silica gel can shorten the detection time.

Width of Absorption Pad

In the following Example 5 and Comparative Examples 5 to 6, the effect on the detection time by the width of the absorption pad and the presence or absence of silica gel was examined by measuring the detection time when the width of the absorption pad was narrowed in the absorption pad containing silica gel or no silica gel.

Example 5

The absorption pad with silica gel containing 70% by weight of silica gel (length: 15 mm, width: 5 mm, thickness: 1 mm supplied from Azumi Filter Paper Co., Ltd.) was prepared, and the laminate was enclosed in the white cassette with an acrylic adhesive tape as shown in FIG. 4 or 5 to make the immunoassay apparatus shown in FIG. 6.

30 µL Of a specimen solution sucked and extracted from a nasal cavity was added onto the specimen dropping part in each apparatus, the developing buffer was supplied by pushing the convex part of the cassette, and the time until the determination line was displayed on the detection site was measured. This was rendered the detection time.

Comparative Example 5

A similar immunoassay apparatus to Example 5 was made by using the wine filter paper having the same size (length: 15 mm, width: 5 mm, thickness: 1 mm) in place of the absorption pad in Example 5. The detection time in this apparatus was measured in the same way as in Example 5.

Comparative Example 6

An immunoassay apparatus was made by using the wine filter paper having the wide width (length: 15 mm, width: 5 mm, thickness: 1 mm) in place of the absorption pad in Example 5 without adhering each member with the seal. The detection time in this apparatus was measured in the same way as in Example 5.

Figure 9:
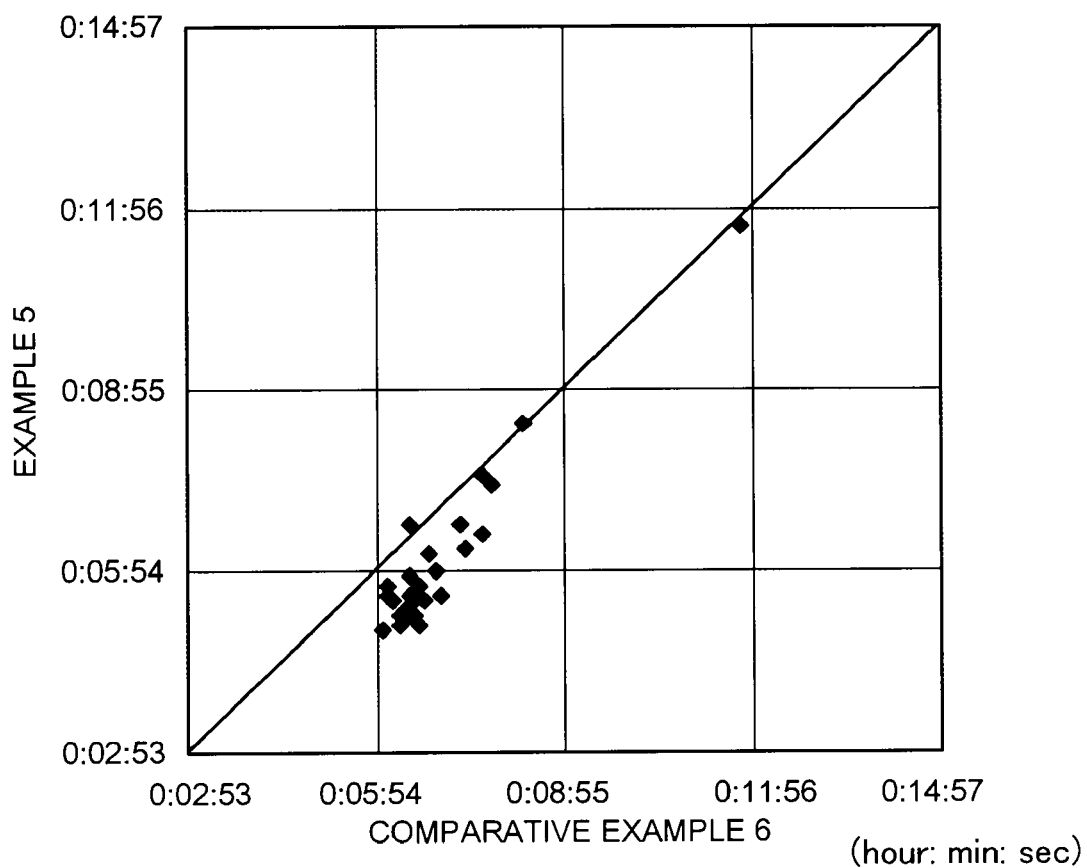
FIG. 9 is a view showing the comparison of the detection time in the immunoassay apparatus using Example 5 with the detection time in the immunoassay apparatus using Comparative Example 6.
Figure 10:
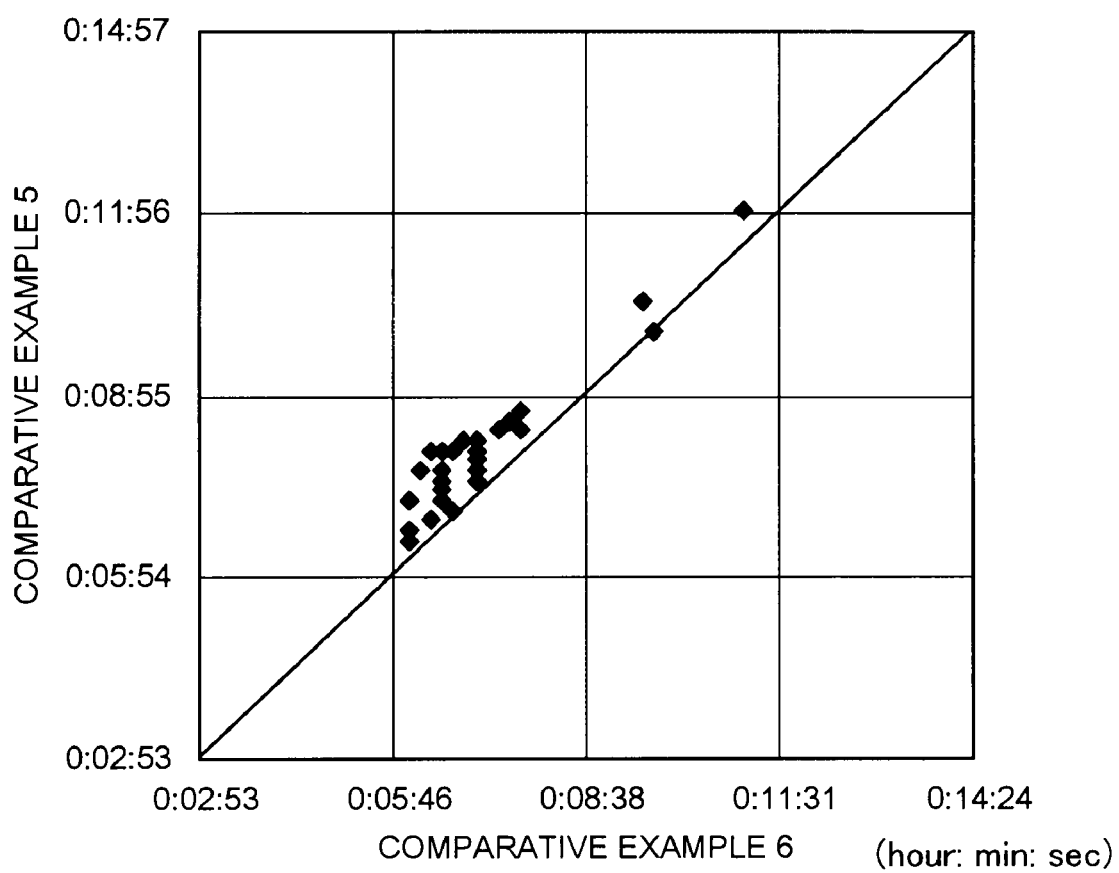
FIG. 10 a view showing the comparison of the detection time in the immunoassay apparatus using Comparative Example 5 with the detection time in the immunoassay apparatus using Comparative Example 6.

The comparison of the detection times between Example 5 and Comparative example 6 is shown in FIG. 9, and the comparison of the detection times between Comparative Example 5 and Comparative example 6 is shown in FIG. 10.

As is shown in FIG. 10, the detection time is longer in Comparative Example 5 than in Comparative Example 6, indicating that the detection time is prolonged by narrowing the width when the absorption pad contains no silica gel. Meanwhile, as shown in FIG. 9, the detection time is longer in Comparative Example 6 than in Example 5. Thus, it is obvious that narrowing the width shortens rather than not prolong the detection time when the silica gel-containing absorption pad is used.

From these results, it has been demonstrated that even when the width of the absorption pad is narrowed to the width suitable for the laminate, the immunoassay apparatus which can detect in a short time is obtained by using the silica gel-containing absorption pad.

Average Particle Diameter of Silica Gel

In the following Examples 6 to 9, the effect on the detection time by the average particle diameter of silica gel was examined.

Example 6

Figure 11:
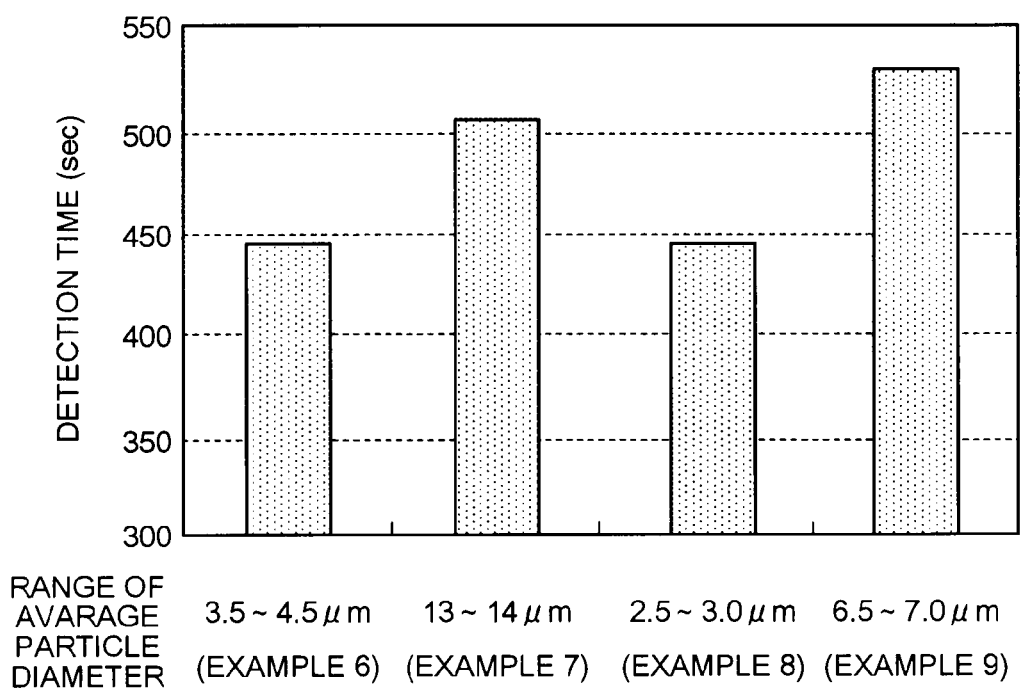
FIG. 11 is a view showing the detection times in the immunoassay apparatuses in Examples 6 to 9.

An absorption pad with silica gel containing 70% by weight of silica gel having the average particle diameter in the range of 3.5 to 4.5 µm (supplied from Azumi Filter Paper Co., Ltd.) was prepared, and the immunoassay apparatus shown in FIG. 6 was made in the same way as in Example 1. The detection time was measured using the same procedure and condition as those in Example 3. The results are shown in FIG. 11.

Example 7

The similar immunoassay apparatus to Example 6 was made by using an absorption pad with silica gel containing 70% by weight of silica gel having the average particle diameter in the range of 13 to 14 µm (supplied from Azumi Filter Paper Co., Ltd.) in place of the absorption pad in Example 6. The detection time in this apparatus was measured in the same way as in Example 6. The results are shown in FIG. 11.

Example 8

The similar immunoassay apparatus to Example 6 was made by using an absorption pad with silica gel containing 70% by weight of silica gel having the average particle diameter in the range of 2.5 to 3 μm (supplied from Azumi Filter Paper Co., Ltd.) in place of the absorption pad in Example 6. The detection time in this apparatus was measured in the same way as in Example 6. The results are shown in FIG. 11.

Example 9

The similar immunoassay apparatus to Example 6 was made by using an absorption pad with silica gel containing 70% by weight of silica gel having the average particle diameter in the range of 6.5 to 7.0 μm (supplied from Azumi Filter Paper Co., Ltd.) in place of the absorption pad in Example 6. The detection time in this apparatus was measured in the same way as in Example 6. The results are shown in FIG. 11.

As is evident from FIG. 11, any of the detection times in respective apparatuses in Examples 6 to 9 is between 7 to 9 minutes. Particularly, the detection time in Example 6 (the range of the average particle diameter was 3.5 to 4.5 μm) and Example 8 (the range of the average particle diameter was 2.5 to 3.0 Mm) was early 7 minutes which was very short.

From these results, it has been demonstrated that according to the immunoassay apparatus using the silica gel-containing absorption pad, the detection can be performed in a short time, and that the detection time can be further shortened by using the absorption pad containing silica gel having the average particle diameter in the range of 4.5 μm or less.

INCORPORATION BY REFERENCE

Each document, patent application or patent publication cited by or referred to in this disclosure is incorporated by reference in its entirety, especially with respect to the subject matter described in the paragraph where the reference is cited and the adjoining paragraphs. However, no admission is made that any such reference constitutes prior art and the right to challenge the accuracy and pertinence of the cited documents is reserved. Any patent document to which this application claims priority is also incorporated by reference in its entirety. Specifically, priority documents PCT/JP2007/054810, filed Mar. 12, 2007 and Japan 2006-068239, filed Mar. 13, 2006 are hereby incorporated by reference.

The invention claimed is:

1. An absorption pad for an immunoassay comprising 50% by weight or more of silicon-containing particles, the silicon-containing particles having a moisture absorptivity of 30% or less at a humidity of 60% or less and a moisture absorptivity of 40% or more at a humidity of 90% or more.

2. The absorption pad for an immunoassay according to claim 1, wherein said silicon-containing particle is silica gel.

3. A strip for an immunoassay for detecting an antigen and/or antibody in a specimen by an antigen-antibody reaction, comprising:
 a labeled form-containing part including a labeled form of an antibody and/or antigen corresponding to the antigen and/or antibody to be detected; and
 a suction part composed of the absorption pad according to claim 1.

4. The strip for an immunoassay according to claim 3 further comprising a substrate-containing part including a substrate to said labeled form.

5. The strip for the immunoassay according to claim 4 wherein said substrate-containing part is located on another end to one end where the suction part is annexed and said labeled form-containing part is located between the substrate-containing part and the suction part.

6. An immunoassay apparatus for measuring an antigen and/or antibody in a specimen by an antigen-antibody reaction, comprising the strip for the immunoassay according to claim 3.

7. The immunoassay apparatus according to claim 6 further comprising a developing buffer supply part for supplying a developing buffer to said strip.

8. A pad comprising
 a material comprising a natural or synthetic polymer compound, and
 silicon-containing particles in an amount of 50% by dry weight or more;
 wherein the silicon-containing particles have a moisture absorptivity of 30% or less at a humidity of 60% and a moisture absorptivity of 40% or more at a humidity of 90% or more.

9. The pad of claim 8, wherein the material comprising a natural or synthetic polymer is a porous material containing polyvinyl alcohol.

10. The pad of claim 8, wherein the material comprising a natural or synthetic polymer is nonwoven.

11. The pad of claim 8, wherein the material comprising a natural or synthetic polymer contains cellulose.

12. The pad of claim 8, wherein the material comprising a natural or synthetic polymer is a sponge or filter paper.

13. The pad of claim 8, wherein the silicon particles have a moisture absorptivity of 20% or less at a humidity of 60% or less.

14. The pad of claim 8, wherein the silicon particles have a moisture absorptivity of 70% or less at a humidity of 95% or more.

* * * * *